(12) United States Patent
Prieditis

(10) Patent No.: US 11,709,910 B1
(45) Date of Patent: Jul. 25, 2023

(54) SYSTEMS AND METHODS FOR IMPUTING MISSING VALUES IN DATA SETS

(71) Applicant: Cigna Intellectual Property, Inc., Wilmington, DE (US)

(72) Inventor: Armand E. Prieditis, Arcata, CA (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 1164 days.

(21) Appl. No.: 16/356,500

(22) Filed: Mar. 18, 2019

(51) Int. Cl.
*G06F 17/10* (2006.01)
*G16H 10/60* (2018.01)
*G06F 40/174* (2020.01)
*G06F 40/18* (2020.01)

(52) U.S. Cl.
CPC ............. *G06F 17/10* (2013.01); *G06F 40/18* (2020.01); *G06F 40/174* (2020.01); *G16H 10/60* (2018.01)

(58) Field of Classification Search
CPC ........ G16H 10/60; G06F 40/18; G06F 40/177; G06F 40/174; G06F 17/10
See application file for complete search history.

(56) References Cited

U.S. PATENT DOCUMENTS

| | | | |
|---|---|---|---|
| 9,838,301 | B2 | 12/2017 | Prieditis |
| 10,097,647 | B2 | 10/2018 | Prieditis |
| 10,142,403 | B1 | 11/2018 | Prieditis |
| 2002/0107858 | A1* | 8/2002 | Lundahl et al. ....... G06Q 30/02 |
| 2014/0280193 | A1* | 9/2014 | Cronin et al. ....... G06F 16/2453 707/741 |
| 2020/0193220 | A1* | 6/2020 | Chen ..................... G06N 20/00 |

FOREIGN PATENT DOCUMENTS

WO 2019153039 A1* 8/2019

OTHER PUBLICATIONS

Bertsimas, et al. (2017). From predictive methods to missing data imputation: an optimization approach. The Journal of Machine Learning Research, 18(1), 7133-7171.
Folch-Fortuny, Abel, Francisco Arteaga, and Alberto Ferrer. "PCA model building with missing data: New proposals and a comparative study." Chemometrics and Intelligent Laboratory Systems 146 (2015): 77-88. (Year: 2015).*
García-Laencina, et al. (Jul. 2006). Pattern classification with missing values using multitask learning. In The 2006 IEEE International Joint Conference on Neural Network Proceedings (pp. 3594-3601). IEEE.
Josse et al. "missMDA: A Package for Handling Missing Values in Multivariate Data Analysis". Journal of Statistical Software Apr. 2016, Volume 70, Issue 1. doi: 10.18637/jss.v070.i01. 31 Pages. (Year: 2016).*
Yoon, et al. Gain: Missing data imputation using generative adversarial nets. arXiv preprint arXiv:1806.02920.; Jun. 7, 2018).

* cited by examiner

*Primary Examiner* — Eunhee Kim
(74) *Attorney, Agent, or Firm* — Harness IP

(57) ABSTRACT

A computer readable medium includes a data set with data stored in rows and N columns. Each of the rows is associated with one individual patient. Each of the N columns is associated with one type of data for patients. One or more processors is configured to: initialize missing values in M ones of the N columns with M values for the M ones of the N columns, respectively; generate M mathematical models for the M ones of the N columns having one or more missing values; for each of the rows having one or more missing values, update ones of the M values for the M ones of the N columns; and fill missing values in the M ones of the N columns with the M values, respectively.

22 Claims, 5 Drawing Sheets

| | Measurement Type 1 | Measurement Type 2 | ... | ICD-10 Code 1 | ICD-10 Code 2 | ... |
|---|---|---|---|---|---|---|
| Patient 1 | 34 | 43 | | F | F | |
| Patient 2 | ? | 12 | | ? | T | |
| Patient 3 | 124 | ? | | T | F | |
| ... | | | | | | |
| Patient X | 34 | 23 | | F | ? | |
| Patient X+1 | 68 | ? | | F | F | |
| Patient X+2 | 114 | 16 | | ? | F | |
| ... | | | | | | |
| Patient Y | 33 | 18 | | T | T | |
| Patient Y+1 | 110 | 23 | | F | F | |
| Patient Y+2 | 63 | 33 | | F | F | |
| ... | | | | | | |

120 — Patient Data
124 — Training Data
128 — Reserved Data

FIG. 2

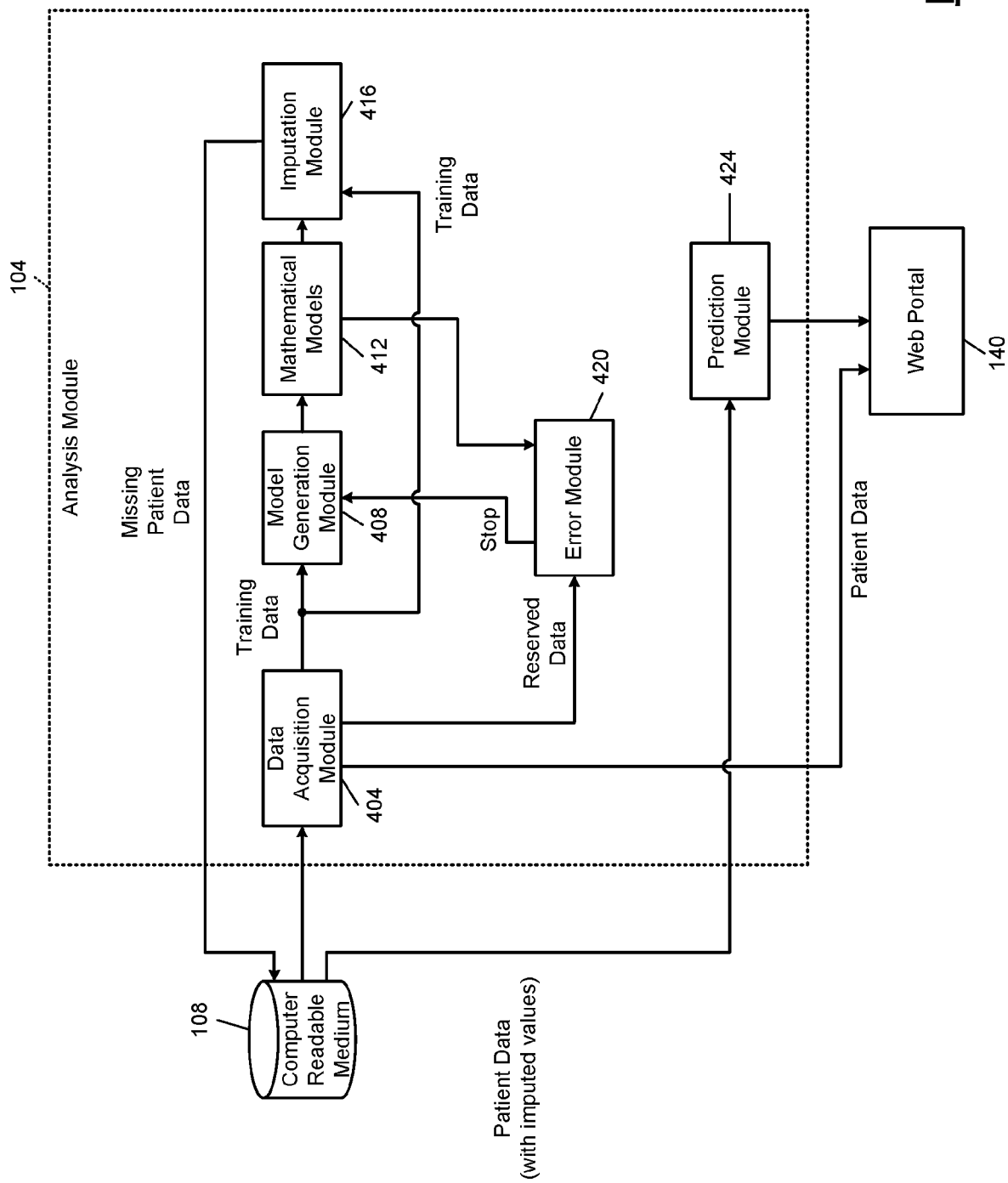

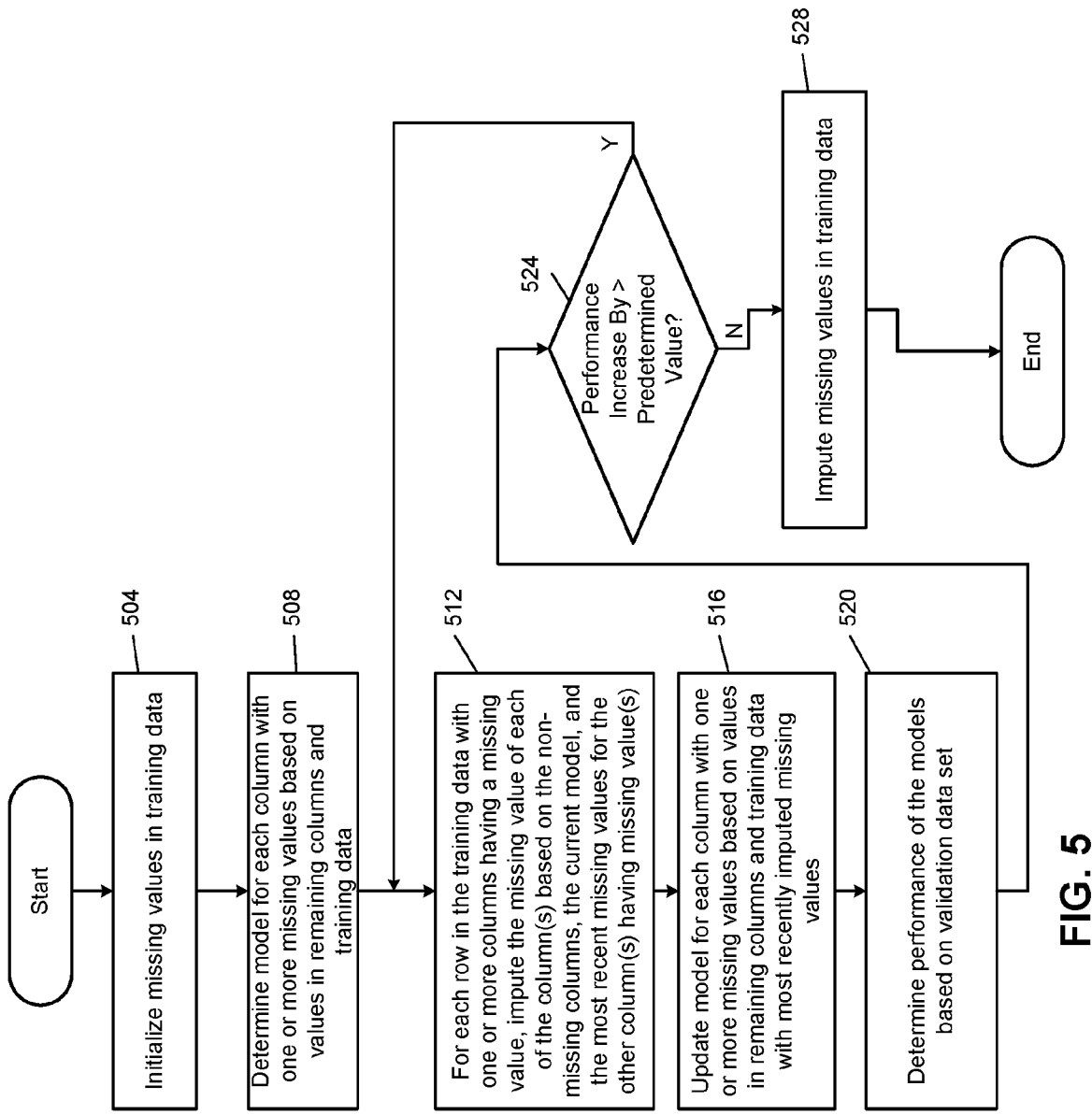

SYSTEMS AND METHODS FOR IMPUTING MISSING VALUES IN DATA SETS

FIELD

The present disclosure relates to systems and methods for imputing missing values in data sets.

BACKGROUND

Some types of data sets may include missing data. For example, an individual's health data may include one or more missing pieces of data. As one example, the individual may not be diagnosed positively or negatively for each different type of disease. Thus, the individual's health data may not include a positive or negative notation for each different ICD-10 (International Statistical Classification of Diseases and Related Health Problems, 10$^{th}$ revision) code.

Even if the individual's health data includes a positive or negative notation for each different ICD-10 code, the individual's health data may not include one or more other types of data. For example, the individual's health data may not include results of one or more different types of laboratory tests or may not include one or more other types of data.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, a system includes: a computer readable medium including a data set with data stored in rows and N columns, where each of the rows is associated with one individual patient, where each of the N columns is associated with one type of data for patients, and where N is an integer greater than one; and one or more processors configured to: (i) initialize missing values in M ones of the N columns in the data set with M values for the M ones of the N columns, respectively, where M is an integer that is greater than zero and less than or equal to N; (ii) generate M mathematical models for the M ones of the N columns of the data set having one or more missing values based on non-missing values of the other ones of the N columns in the data set; (iii) for each of the rows of the data set having one or more missing values, update ones of the M values for the M ones of the N columns based on non-missing values of that row of the data set, the ones of the M mathematical models, respectively, and ones of the M values for other ones of the M ones of the N columns with missing values; and (vi) fill missing values in the M ones of the N columns in the data set with the M values, respectively.

In further features, the one or more processors are configured to generate a prediction based on data in at least one row of the data set, where the at least one row of the data set is filled with at least one of the M values.

In further features, at least one of the M ones of the N columns includes categorical data that is limited to being in a first state, in a second state, or missing.

In further features, at least one of the M ones of the N columns includes continuous data that is within a range of values or missing.

In further features, the one or more processors are further configured to determine an error value based on the M values and to selectively repeat (iii) and (iv) based on the error value.

In further features, the one or more processors are configured to determine the error value using a root mean square error (RMSE) function.

In further features: the computer readable medium further includes a second data set with reserved data stored in rows and N columns; and the one or more processors are configured to determine the error value further based on the second data set.

In further features, the one or more processors are further configured to, after (iii), update the M mathematical models.

In a feature, a system includes a database including: a first data set with data stored in rows and N columns, where each of the rows is associated with one individual patient, where each of the N columns is associated with one type of data for patients, and where N is an integer greater than one; and a second data set with reserved data stored in rows and N columns. One or more processors are configured to: (i) initialize missing values in M ones of the N columns in the first data set with M values for the M ones of the N columns, respectively, where M is an integer that is greater than zero and less than or equal to N; (ii) generate M mathematical models for the M ones of the N columns of the first data set having one or more missing values based on non-missing values of the other ones of the N columns in the first data set; (iii) for each of the rows of the first data set having one or more missing values, update ones of the M values for the M ones of the N columns based on non-missing values of that row of the first data set, the ones of the M mathematical models, respectively, and ones of the M values for other ones of the M ones of the N columns with missing values; (iv) update each one the M mathematical models for the M ones of the N columns based on values in other ones of the N columns, the first data set, and the M values; (v) determine a performance value for the M mathematical models based on the M values and the second data set; (vi) repeat (iii) - (v) when an increase in the performance value is greater than a predetermined value; and (vii) when the increase in the performance value is not greater than the predetermined value, fill missing values in the M ones of the N columns in the first data set with the M values, respectively.

In further features, the one or more processors are configured to generate a prediction based on data in at least one row of the first data set, where the at least one row of the first data set is filled with at least one of the M values.

In further features, at least one of the M ones of the N columns includes categorical data that is limited to being in a first state, in a second state, or missing.

In further features, at least one of the M ones of the N columns includes continuous data that is within a range of values or missing.

In further features, the one or more processors are configured to determine the performance value using a root mean square error (RMSE) function.

In a feature, a method includes: by one or more processors, selectively retrieving, from a database, a data set with patient data stored in rows and N columns, where each of the rows is associated with one individual patient, where each of the N columns is associated with one type of data for patients, and where N is an integer greater than one; by the one or more processors, (i) initializing missing values in M ones of the N columns in the data set with M values for the M ones of the N columns, respectively, where M is an integer that is greater than zero and less than or equal to N; by the one or more processors, (ii) generating M mathematical models for the M ones of the N columns of the data set having one or more missing values based on non-missing values of the other ones of the N columns in the data set; by the one or more processors, (iii) for each of the rows of the data set having one or more missing values, updating ones of the M values for the M ones of the N columns based on non-missing values of that row of the data set, the ones of the M mathematical models, respectively, and ones of the M values for other ones of the M ones of the N columns with missing values; and by the one or more processors, (vi) filling missing values in the M ones of the N columns in the data set with the M values, respectively.

In further features, the method further includes, by the one or more processors, generating a prediction based on data in at least one row of the data set, where the at least one row of the data set is filled with at least one of the M values.

In further features, at least one of the M ones of the N columns includes categorical data that is limited to being in a first state, in a second state, or missing.

In further features, at least one of the M ones of the N columns includes continuous data that is within a range of values or missing.

In further features, the method further includes: by the one or more processors, determining an error value based on the M values; and selectively repeating (iii) and (iv) based on the error value.

In further features, determining the error value includes, by the one or more processors, determining the error value using a root mean square error (RMSE) function.

In further features, the method further includes: by the one or more processors, selectively retrieving, from the database, a second data set with reserved data stored in rows and N columns; and by the one or more processors, determining the error value further based on the second data set.

In further features, the method further includes, by the one or more processors, update the M mathematical models.

In a feature, a non-transitory computer-readable medium stores processor-executable instructions that, when executed by one or more processors, perform functions comprising: selectively retrieving, from a database: a first data set with patient data stored in rows and N columns, where each of the rows is associated with one individual patient, where each of the N columns is associated with one type of data for patients, and where N is an integer greater than one; and a second data set with reserved data stored in rows and N columns; (i) initializing missing values in M ones of the N columns in the first data set with M values for the M ones of the N columns, respectively, where M is an integer that is greater than zero and less than or equal to N; (ii) generating M mathematical models for the M ones of the N columns of the first data set having one or more missing values based on non-missing values of the other ones of the N columns in the first data set; (iii) for each of the rows of the first data set having one or more missing values, updating ones of the M values for the M ones of the N columns based on non-missing values of that row of the first data set, the ones of the M mathematical models, respectively, and ones of the M values for other ones of the M ones of the N columns with missing values; and (vi) filling missing values in the M ones of the N columns in the first data set with the M values, respectively.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 2 is an illustration of an example data set.

FIG. 4 is a functional block diagram including an example implementation of an analysis module.

FIG. 5 includes a flowchart depicting an example method of imputing missing values.

In the drawings, reference numbers may be reused to identify similar and/or identical elements.

DETAILED DESCRIPTION

Missing values in a set of data can be imputed, for example, by interpolation of non-missing values, by averaging the non-missing values, by determining a median of the non-missing values, etc. Alternatively, rows with missing values can be removed from consideration.

These methods, however, may provide insufficient performance. For example, filling missing values with a mean of the non-missing values may pull everything towards the mean, which may decrease a value of the data in that column. If most of the rows of the data set have missing values in a column, most of the rows of the data set will have the same value in that column if the missing values of that column are all filled with a mean of the non-missing values of that column. This may decrease an efficacy of machine learning using the data in that column.

The present application involves imputation of missing values. First, initial values for missing values of a row are determined. As an example, the most likely value may be used. For example, for values of columns including categorical values (T or F, 1 or 0, etc.), the initial values can be filled in randomly and based on a frequency distribution of the non-missing values of that column. For values of columns including continuous values, the initial values can be filled in randomly based on a mean and a variance of the non-missing values of that column. Categorical values can only be in a first state (e.g., T), a second state (e.g., F), or missing. Continuous values are within a range or missing.

Second, a prediction engine (mathematical model) is built for each column based on the data in one or more of the other columns. For a data set including k columns of different types of data, there can be k prediction engines.

Third, for each missing column in a particular row, the prediction engine of that column predicts the missing value for that column based on the current prediction engine and the remaining columns for that row. Fourth, the prediction engines are updated. After all of the rows have been processed as described, the prediction engines are updated based on the values generated by the other prediction engines of the other columns.

Fifth, an error metric can be determined based on the rows including the updated missing values. The process may be repeated (second – fifth) until the error metric converges on a reserved test set.

The method of filling missing values described herein is not tied to a specific type of machine learning (ML). Thus, various different ML toolkits may be used. For example, Data Robot or sci-kit learn may be used. Multiple different ML toolkits can be used in any one iteration and can change from iteration to iteration.

Figure 1:
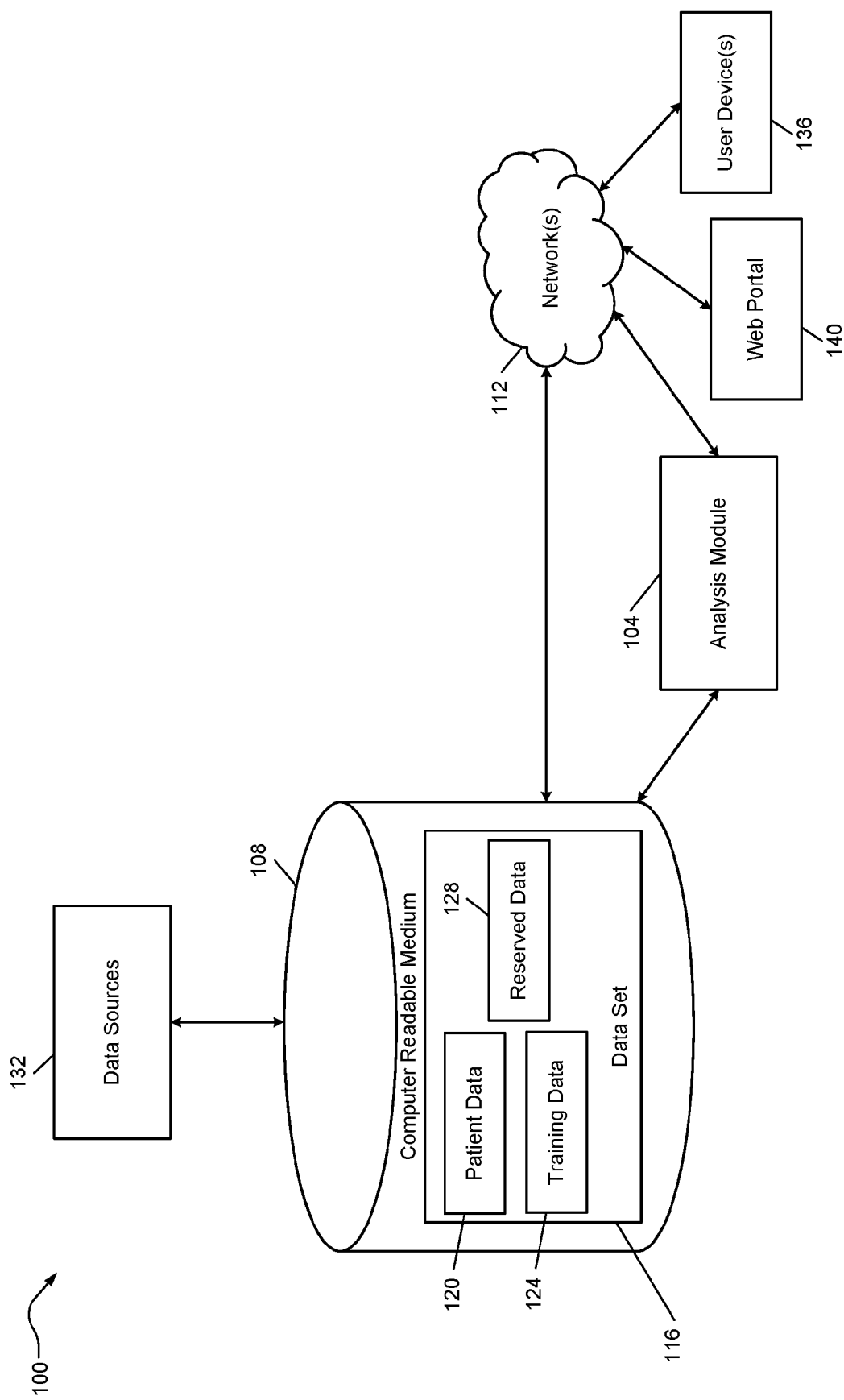
FIG. 1 is a functional block diagram of an example system for imputing missing values.

FIG. 1 is a block diagram of an example imputation system 100. While the imputation system 100 is generally described as imputing patient data, the imputation system 100 may also be used to impute missing values in other types of data. The imputation system 100 may include an analysis module 104 and a computer readable medium 108 in communication with each other directly and/or over a network 112.

The computer readable medium 108 stores a data set 116. The data set 116 includes patient data 120, training data 124, and reserved data 128. FIG. 2 includes an example illustration of the data set 116 including examples of the patient data 120, the training data 124, and the reserved data 128. In the example of FIG. 2, question marks (?) indicate missing values in the data.

The data set 116 may be arranged in rows and columns. In an example, each row is associated with one specific patient. For example, the patient data 120 is illustrated as including a first row for a first patient (Patient 1), a second row for a second patient (Patient 2), etc. The training data 124 is also illustrated as including a row for an X-th patient (Patient X), an X+1th patient (Patient X + 1), etc. The reserved data 128 is also illustrated as including a row for a Y-th patient (Patient Y), a row for a Y+1th patient (Patient Y+1), etc. The patient data 120 may have the same or a different number of rows than the training data 124. The training data 124 may have the same or a different number of rows than the reserved data 128. The patient data 120 may have the same or a different number of rows than the reserved data 128.

Each column includes one type of data for the patients. For example, a first column (Measurement Type 1) may include a first type of measurements of the patients, respectively, a second column (Measurement Type 2) may include a second type of measurements of the patients, respectively, etc. A third column (ICD-10 code 1) includes indicators of whether the patients have a first medical condition associated with a first ICD-10 code, a fourth column (ICD-10 code 2) includes indicators of whether the patients have a second medical condition associated with a second ICD-10 code, etc.

While the examples of measurements and ICD-10 codes are provided, the data set 116 may include one or more columns for one or more other types of data associated with the rows. Also, while the example of patient (medical) data is provided, the data set 116 may include other types of data. In various implementations, each column may be associated with one specific patient, and each row may include one type of data for the patients.

One or more data sources 132 store and update the patient data 120. For example, a data source may add a row to the patient data 120 for a patient that does not presently have a row in the patient data 120 is to be stored. The data source stores the data for the patient in the added row and the appropriate column(s) for the data. If data is received for a patient that does presently have a row in the patient data 120, the data source may add the data for the patient to the appropriate column(s) for the data. The data sources 132 may include, for example, computing devices of the patients, computing devices of health care professionals serving the patients, and other types of data sources.

The imputation system 100 may also include one or more user device(s) 136. A user, such as a pharmacist, patient, data analyst, health plan administrator, etc., may access the data stored in the computer readable medium 108 using the user device 136. The user device 136 may be a desktop computer, a laptop computer, a tablet, a smartphone, etc.

Figure 3:
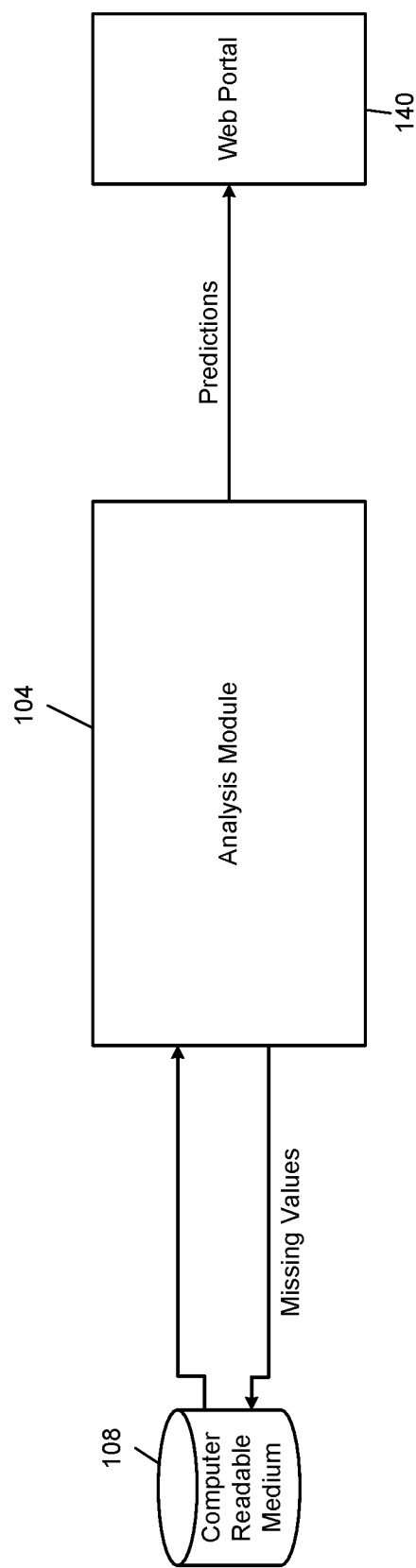
FIG. 3 is a functional block diagram including an example illustration of a computer readable medium, an analysis module, and a web portal.

FIG. 3 includes a functional block diagram including an example illustration of the computer readable medium 108, the analysis module 104, and a web portal 140. As discussed further below, the analysis module 104 fills missing values in the patient data 120. The analysis module 104 fills the missing values using the training data 124 and the reserved data 128. Once the missing values in the patient data 120 are filled, the analysis module 104 generates one or more predictions based on the (then filled) patient data 120 or the (then filled) training data 124 including the values that were previously missing.

The computer readable medium 108 may include non-transitory storage, such as memory, a hard disk, a CD-ROM, etc. The patient data 120, the training data 124, and the reserved data 128 may be stored in the non-transitory storage. Further, the imputation system 100 may include additional devices, which may communicate with each other directly or over the network 112.

The prediction(s) and/or data stored in the computer readable medium 108 may be accessible by the web portal 140. The web portal 140 may generate interfaces that display and organize data. The web portal 140 may generate a user interface for each user that logs on to the web portal 140. When a user logs on to the web portal 140, the web portal 140 may access data associated with the user and may display the associated data in the user interface.

FIG. 4 is a functional block diagram including an example implementation of the analysis module 104.

A data acquisition module 404 retrieves data from the computer readable medium 108. For example, the data acquisition module 404 may selectively retrieve the patient data 120, the training data 124, and/or the reserved data 128.

A model generation module 408 generates mathematical models 412 (prediction engines) for each column. The mathematical model 412 for a column generates a predicted value for missing values in that column. An example mathematical model 412 for a first column includes:

$$P1 = (W2*P2) + ...(Wm*Pm),$$

where P1 is the predicted value for the first column (1), m is an integer greater than 1, P2 is the predicted value for a second column generated by the mathematical model for the second column, W2 is a weight value for the second column, Pm is the predicted value for an m-th column generated by the mathematical model for the m-th column, and Wm is a weighting value for the m-th column. In this example, (W2 * P2)+ ... (Wm * Pm) is the mathematical model. While one example mathematical model is provided, another suitable mathematical model may be used.

An imputation module 416 fills missing values of the columns with the (predicted) values generated by the mathematical models 412 of the columns, respectively.

An error module 420 determines error values for the columns based on differences between the values generated by the mathematical models 412 of the columns and values generated by the mathematical models 412 based on the values in the same columns of the reserved data 128, respectively. For example, the error module 420 may determine the error values for the columns using a root mean square error (RSME) or another suitable error metric.

The model generation module 408 may iteratively update ones of the mathematical models 412 until the error values of the columns become less than a predetermined value or decrease by less than a predetermined amount. In the example above, one or more of the weighting values may be adjusted. The mathematical models 412 may be updated in parallel, such as using pyspark. In this regard, the data may be stored in the computer readable medium 108 using a python matrix or pandas instead of writing and reading intermediate files. Writing and reading intermediate files may slow the process of updating ones of the mathematical models 412.

Once the error values of the columns has become less than the predetermined value or decreased by less than the predetermined amount, the imputation module 416 may fill missing values of the columns in the patient data 120 with the values generated by the mathematical models 412 of the columns, respectively. For example, the imputation module 416 fills missing values of a first column in the patient data 120 with the value generated by the one of the mathematical models 412 of the first column.

A prediction module 424 generates one or more predicted values based on the patient data 120 with the missing values filled. For example, the prediction module 424 may predict a cost value, predict a likelihood of patients having a condition, or generate another type of predicted value based on the patient data 120 with the missing values filled.

FIG. 5 includes a flowchart depicting an example method of imputing missing values. Control begins with 504 where the imputation module 416 initializes missing values in the columns of the training data 124 with most likely values for the rows, respectively. For example, for columns including categorical values (T or F, 1 or 0, etc.), the imputation module 416 may initialize missing values randomly to achieve the same frequency distribution as the non-missing values of that column. For values of columns including continuous values, the initial values can be filled in randomly to achieve the same mean and variance of the non-missing values of that column.

At 508, the model generation module 408 generates the mathematical models 412 for the columns, respectively, of the training data 124. The model generation module 408 generates the mathematical model 412 for a column based on the values in the other columns of the training data 124. Each of the mathematical models 412 generates a predicted value for its associated column based on the values predicted by one, more than one, or all of the other mathematical models 412.

At 512, for each row of the training data 124 including one or more missing values (in one or more of the columns), the imputation module 416 imputes (fills) the missing value of each of columns in the training data 124 based on the values of the columns with non-missing values, the present mathematical model for that column, and the most recent values of the mathematical models of the other columns.

At 516, the model generation module 408 updates the mathematical models 412 of the columns with one or more missing values, respectively, based on the values on the other columns of the training data 124. At 520, the error module 420 determines the error values for the columns, respectively, based on the values generated by the models 412 based on the training data 124 and values determined based on the corresponding columns of the reserved data 128. For example, the error module 420 may determine the error value using RSME or another suitable error metric. The error value reflects a performance of the mathematical models 412.

At 524, the error module 420 may determine whether the error value is greater than the predetermined value or did not decrease by at least the predetermined amount. Alternatively, the error module 420 may determine whether performance of the models 412 increased by at least a predetermined amount at 524. If 524 is true, control returns to 512 to continue the process and update the mathematical models 412 again. If 524 is false, control continues with 528.

At 528, the imputation module 416 imputes (fills/stores) missing values in columns of the training data 120 with the values generated by the mathematical models 412 of the columns, respectively. The prediction module 424 may generate one or more predictions based on the training data 120 with the missing values imputed/filled.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system comprising:
    a computer readable medium including a data set with data stored in rows and N columns,
        wherein each of the rows is associated with one individual patient,
        wherein each of the N columns is associated with one type of data for patients, and
        wherein N is an integer greater than one; and
    one or more processors configured to:
        (i) initialize missing values in M ones of the N columns in the data set with M values for the M ones of the N columns, respectively,
            wherein M is an integer that is greater than zero and less than or equal to N;
        (ii) generate M mathematical models for the M ones of the N columns of the data set having one or more missing values, respectively, based on non-missing values of the other ones of the N columns in the data set;
        (iii) for each of the rows of the data set having one or more missing values, update ones of the M values for the M ones of the N columns based on non-missing values of that row of the data set, the ones of the M mathematical models, respectively, and ones of the M values for other ones of the M ones of the N columns with missing values; and
        (iv) fill missing values in the M ones of the N columns in the data set with the M values, respectively.

2. The system of claim 1 wherein the one or more processors are configured to generate a prediction based on data in at least one row of the data set, wherein the at least one row of the data set is filled with at least one of the M values.

3. The system of claim 1 wherein at least one of the M ones of the N columns includes categorical data that is limited to being in a first state, in a second state, or missing.

4. The system of claim 1 wherein at least one of the M ones of the N columns includes continuous data that is within a range of values or missing.

5. The system of claim 1 wherein the one or more processors are further configured to determine an error value based on the M values and to selectively repeat (iii) and (iv) based on the error value.

6. The system of claim 5 wherein the one or more processors are configured to determine the error value using a root mean square error (RMSE) function.

7. The system of claim 5 wherein:
the computer readable medium further includes a second data set with reserved data stored in rows and N columns; and
the one or more processors are configured to determine the error value further based on the second data set.

8. The system of claim 1 wherein the one or more processors are further configured to, after (iii), update the M mathematical models.

9. A system comprising:
a database including:
a first data set with data stored in rows and N columns,
wherein each of the rows is associated with one individual patient,
wherein each of the N columns is associated with one type of data for patients, and
wherein N is an integer greater than one; and
a second data set with reserved data stored in rows and N columns; and
one or more processors configured to:
(i) initialize missing values in M ones of the N columns in the first data set with M values for the M ones of the N columns, respectively,
wherein M is an integer that is greater than zero and less than or equal to N;
(ii) generate M mathematical models for the M ones of the N columns of the first data set having one or more missing values, respectively, based on non-missing values of the other ones of the N columns in the first data set;
(iii) for each of the rows of the first data set having one or more missing values, update ones of the M values for the M ones of the N columns based on non-missing values of that row of the first data set, the ones of the M mathematical models, respectively, and ones of the M values for other ones of the M ones of the N columns with missing values,
(iv) update each one the M mathematical models for the M ones of the N columns based on values in other ones of the N columns, the first data set, and the M values;
(v) determine a performance value for the M mathematical models based on the M values and the second data set;
(vi) repeat (iii) - (v) when an increase in the performance value is greater than a predetermined value; and
(vii) when the increase in the performance value is not greater than the predetermined value, fill missing values in the M ones of the N columns in the first data set with the M values, respectively.

10. The system of claim 9 wherein the one or more processors are configured to generate a prediction based on data in at least one row of the first data set,
wherein the at least one row of the first data set is filled with at least one of the M values.

11. The system of claim 9 wherein at least one of the M ones of the N columns includes categorical data that is limited to being in a first state, in a second state, or missing.

12. The system of claim 9 wherein at least one of the M ones of the N columns includes continuous data that is within a range of values or missing.

13. The system of claim 9 wherein the one or more processors are configured to determine the performance value using a root mean square error (RMSE) function.

14. A method comprising:
by one or more processors, selectively retrieving, from a database, a data set with patient data stored in rows and N columns,
wherein each of the rows is associated with one individual patient,
wherein each of the N columns is associated with one type of data for patients, and
wherein N is an integer greater than one; and
by the one or more processors, (i) initializing missing values in M ones of the N columns in the data set with M values for the M ones of the N columns, respectively,
wherein M is an integer that is greater than zero and less than or equal to N;
by the one or more processors, (ii) generating M mathematical models for the M ones of the N columns of the data set having one or more missing values, respectively, based on non-missing values of the other ones of the N columns in the data set;
by the one or more processors, (iii) for each of the rows of the data set having one or more missing values, updating ones of the M values for the M ones of the N columns based on non-missing values of that row of the data set, the ones of the M mathematical models, respectively, and ones of the M values for other ones of the M ones of the N columns with missing values; and
by the one or more processors, (iv) filling missing values in the M ones of the N columns in the data set with the M values, respectively.

15. The method of claim 14 further comprising, by the one or more processors, generating a prediction based on data in at least one row of the data set,
wherein the at least one row of the data set is filled with at least one of the M values.

16. The method of claim 14 wherein at least one of the M ones of the N columns includes categorical data that is limited to being in a first state, in a second state, or missing.

17. The method of claim 14 wherein at least one of the M ones of the N columns includes continuous data that is within a range of values or missing.

18. The method of claim 14 further comprising:
by the one or more processors, determining an error value based on the M values; and
selectively repeating (iii) and (iv) based on the error value.

19. The method of claim 18 wherein determining the error value includes, by the one or more processors, determining the error value using a root mean square error (RMSE) function.

20. The method of claim 18 further comprising:
by the one or more processors, selectively retrieving, from the database, a second data set with reserved data stored in rows and N columns; and
by the one or more processors, determining the error value further based on the second data set.

21. The method of claim 14 further comprising, by the one or more processors, update the M mathematical models.

22. A non-transitory computer-readable medium storing processor-executable instructions that, when executed by one or more processors, perform functions comprising:
- selectively retrieving, from a database:
  - a first data set with patient data stored in rows and N columns,
  - wherein each of the rows is associated with one individual patient,
  - wherein each of the N columns is associated with one type of data for patients,
  - and wherein N is an integer greater than one; and
  - a second data set with reserved data stored in rows and N columns;
- (i) initializing missing values in M ones of the N columns in the first data set with M values for the M ones of the N columns, respectively,
- wherein M is an integer that is greater than zero and less than or equal to N;
- (ii) generating M mathematical models for the M ones of the N columns of the first data set having one or more missing values, respectively, based on non-missing values of the other ones of the N columns in the first data set;
- (iii) for each of the rows of the first data set having one or more missing values, updating ones of the M values for the M ones of the N columns based on non-missing values of that row of the first data set, the ones of the M mathematical models, respectively, and ones of the M values for other ones of the M ones of the N columns with missing values; and
- (iv) filling missing values in the M ones of the N columns in the first data set with the M values, respectively.

\* \* \* \* \*